(12) United States Patent
Zwick et al.

(10) Patent No.: US 10,113,254 B2
(45) Date of Patent: Oct. 30, 2018

(54) DISPERSIBLE MOIST WIPE

(71) Applicant: Kimberly-Clark Worldwide, Inc., Neenah, WI (US)

(72) Inventors: Kenneth John Zwick, Neenah, WI (US); Nathan John Vogel, Neenah, WI (US); Joseph Kenneth Baker, Cumming, GA (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 581 days.

(21) Appl. No.: 14/068,847

(22) Filed: Oct. 31, 2013

(65) Prior Publication Data
US 2015/0118466 A1 Apr. 30, 2015

(51) Int. Cl.
| | |
|---|---|
| *D04H 1/04* | (2012.01) |
| *A61K 8/02* | (2006.01) |
| *A61F 13/15* | (2006.01) |
| *D04H 1/425* | (2012.01) |
| *D04H 1/4258* | (2012.01) |
| *D04H 1/492* | (2012.01) |

(52) U.S. Cl.
CPC ......... *D04H 1/04* (2013.01); *A61F 13/15211* (2013.01); *A61K 8/0208* (2013.01); *D04H 1/425* (2013.01); *D04H 1/4258* (2013.01); *D04H 1/492* (2013.01); *Y10T 442/608* (2015.04); *Y10T 442/689* (2015.04)

(58) Field of Classification Search
CPC ... A61K 8/0208; A61F 13/15211; D04H 1/04; D04H 1/4258; D04H 1/492; D04H 1/425; Y10T 442/689; Y10T 442/608
USPC ................................ 428/219; 442/408, 334
See application file for complete search history.

(56) References Cited

U.S. PATENT DOCUMENTS

| | | | |
|---|---|---|---|
| 4,117,187 | A | 9/1978 | Adams et al. |
| 4,755,421 | A | 7/1988 | Manning et al. |
| 5,009,747 | A | 4/1991 | Viazmensky et al. |
| 5,281,306 | A | 1/1994 | Kakiuchi et al. |
| 5,292,581 | A | 3/1994 | Viazmensky et al. |
| 5,770,528 | A | 6/1998 | Mumick et al. |
| 5,935,880 | A | 8/1999 | Wang et al. |
| 5,976,694 | A | 11/1999 | Tsai et al. |
| 5,986,004 | A | 11/1999 | Pomplun et al. |
| 6,043,317 | A | 3/2000 | Mumick et al. |

(Continued)

FOREIGN PATENT DOCUMENTS

| | | |
|---|---|---|
| CN | 102665510 A | 9/2012 |
| EP | 0608460 | 8/1994 |

(Continued)

OTHER PUBLICATIONS

Kohlhammer, "New airlaid binders"; Nonwovens Report International; Sep. 1999; pp. 20-22; 28-31; Issue 342.

(Continued)

*Primary Examiner* — Brian Handville
(74) *Attorney, Agent, or Firm* — Armstrong Teasdale LLP (57) ABSTRACT

A dispersible moist wipe generally comprises a nonwoven tissue web having regenerated fibers in an amount of about 10 to about 30 percent by weight and natural fibers in an amount of about 70 to about 90 percent by weight. The regenerated fibers and the natural fibers are hydroentangled such that the web has a geometric mean tensile strength of at least 250 grams per inch and a slosh-box break-up time of less than 155 minutes.

30 Claims, 7 Drawing Sheets

(56) References Cited

U.S. PATENT DOCUMENTS

| | | |
|---|---|---|
| 6,110,848 A | 8/2000 | Bouchette |
| 6,537,663 B1 | 3/2003 | Chang et al. |
| 6,994,865 B2 | 2/2006 | Branham et al. |
| 7,588,663 B2 | 9/2009 | Skoog et al. |
| 7,732,357 B2 | 6/2010 | Annis et al. |
| 2002/0081930 A1 | 6/2002 | Jackson et al. |
| 2002/0111450 A1 | 8/2002 | Chang et al. |
| 2002/0155281 A1 | 10/2002 | Lang et al. |
| 2003/0026963 A1 | 2/2003 | Chang et al. |
| 2004/0013859 A1 | 1/2004 | Annis et al. |
| 2004/0055704 A1 | 3/2004 | Bunyard et al. |
| 2004/0058606 A1 | 3/2004 | Branham et al. |
| 2005/0266759 A1 | 12/2005 | Baer et al. |
| 2006/0147505 A1 | 7/2006 | Tanzer et al. |
| 2007/0226970 A1 | 10/2007 | Pourdeyhimi et al. |
| 2008/0076313 A1 | 3/2008 | Uitenbroek et al. |
| 2011/0290437 A1 | 12/2011 | Vogel et al. |
| 2012/0297560 A1 | 11/2012 | Zwick et al. |
| 2013/0198984 A1 | 8/2013 | Strandqvist et al. |
| 2014/0170402 A1 | 6/2014 | Knowlson et al. |

FOREIGN PATENT DOCUMENTS

| | | |
|---|---|---|
| EP | 2441869 A1 | 4/2012 |
| JP | 5179548 | 7/1993 |
| JP | 9228214 | 9/1997 |
| JP | 10310960 | 11/1998 |
| JP | 11012909 | 1/1999 |
| JP | 11043854 | 2/1999 |
| JP | 11093055 | 4/1999 |
| WO | 2013103844 A1 | 7/2013 |

OTHER PUBLICATIONS

International Search Report and Written Opinion of International Application No. PCT/IB2014/065279; dated Feb. 6, 2015; 14 pages.

Soukupova, V. et al., Studies on the Properties of Biodegradable Wipes made by the Hydroentanglement Bonding Technique, Textile Research Journal, 2007, pp. 301-311, vol. 77, No. 5.

Extended European Search Report for Application No. 14859096.1, dated May 3, 2017, 8 pages.

DISPERSIBLE MOIST WIPE

FIELD

The field of the invention relates generally to moist wipes and more specifically to dispersible moist wipes adapted to be flushed down a toilet and methods of making such moist wipes.

BACKGROUND

Dispersible moist wipes are generally intended to be used and then flushed down a toilet. Accordingly, it is desirable for such flushable moist wipes to have an in-use strength sufficient to withstand a user's extraction of the wipe from a dispenser and the user's wiping activity, but then relatively quickly breakdown and disperse in household and municipal sanitization systems, such as sewer or septic systems. Some municipalities may define "flushable" through various regulations. Flushable moist wipes must meet these regulations to allow for compatibility with home plumbing fixtures and drain lines, as well as the disposal of the product in onsite and municipal wastewater treatment systems.

One challenge for some known flushable moist wipes is that it takes a relatively longer time for them to break down in a sanitation system as compared to conventional, dry toilet tissue thereby creating a risk of blockage in toilets, drainage pipes, and water conveyance and treatment systems. Dry toilet tissue typically exhibits lower post-use strength upon exposure to tap water, whereas some known flushable moist wipes require a relatively long period of time and/or significant agitation within tap water for their post-use strength to decrease sufficiently to allow them to disperse. Attempts to address this issue, such as making the wipes to disperse more quickly, may reduce the in-use strength of the flushable moist wipes below a minimum level deemed acceptable by users.

Some known flushable moist wipes are formed by entangling fibers in a nonwoven web. A nonwoven web is a structure of individual fibers which are interlaid to form a matrix, but not in an identifiable repeating manner. While the entangled fibers themselves may disperse relatively quickly, known wipes often require additional structure to improve in-use strength. For example, some known wipes use a net having fibers entangled therewith. The net provides additional cohesion to the entangled fibers for an increased in-use strength. However, such nets do not disperse upon flushing.

Some known moist wipes obtain increased in-use strength by entangling bi-component fibers in the nonwoven web. After entanglement, the bi-component fibers are thermoplastically bonded together to increase in-use strength. However, the thermoplastically bonded fibers negatively impact the ability of the moist wipe to disperse in a sanitization system in a timely fashion. That is, the bi-component fibers and thus the moist wipe containing the bi-component fibers often do not readily disperse when flushed down a toilet.

Other known flushable moist wipes add a triggerable salt-sensitive binder. The binder attaches to the cellulose fibers of the wipes in a formulation containing a salt solution, yielding a relatively high in-use strength. When the used moist wipes are exposed to the water of the toilet and/or sewer system, the binder swells thereby allowing and potentially even assisting in the wipes falling apart, which allows for relatively rapid dispersal of the wipes. However, such binders are relatively costly.

Still other known flushable moist wipes incorporate a relatively high quantity of synthetic fibers to increase the in-use strength. However, the ability of such wipes to disperse in a timely fashion is correspondingly reduced. In addition, a higher cost of synthetic fibers relative to natural fibers causes a corresponding increase in cost of such known moist wipes.

Thus, there is a need to provide a wet wipe made from a dispersible nonwoven tissue web that provides an in-use strength expected by consumers, disperses sufficiently quickly to be flushable without creating potential problems for household and municipal sanitation systems, and is cost-effective to produce.

BRIEF DESCRIPTION

In one aspect, a dispersible moist wipe generally comprises a nonwoven tissue web having regenerated fibers in an amount of about 10 to about 30 percent by weight and natural fibers in an amount of about 70 to about 90 percent by weight. The regenerated fibers and the natural fibers are hydroentangled such that the web has a geometric mean tensile strength of at least 250 grams per inch and a slosh-box break-up time of less than 155 minutes.

In another aspect, a dispersible moist wipe generally comprises a nonwoven tissue web having regenerated fibers in an amount of about 10 to about 30 percent by weight and natural fibers in an amount of about 70 to about 90 percent by weight. The regenerated fibers and the natural fibers are hydroentangled such that the web has a geometric mean tensile strength of at least 250 grams per inch and a shaker flask pass-through percentage value at a 12 millimeter screen of at least 60 percent.

In yet another aspect, a dispersible moist wipe generally comprises a nonwoven tissue web comprising regenerated fibers having a length in the range of about 4 millimeters to about 15 millimeters and natural fibers having a length greater than about 1 millimeter. The regenerated fibers and the natural fibers are hydroentangled such that the web has a geometric mean tensile strength of at least 350 grams per inch.

DETAILED DESCRIPTION OF THE DRAWINGS

The dispersible moist wipes of the current disclosure have sufficient strength to withstand packaging and consumer use. They also disperse sufficiently quickly to be flushable without creating potential problems for household and municipal sanitation systems. Additionally, they may be comprised of materials that are suitably cost-effective.

Figure 1:
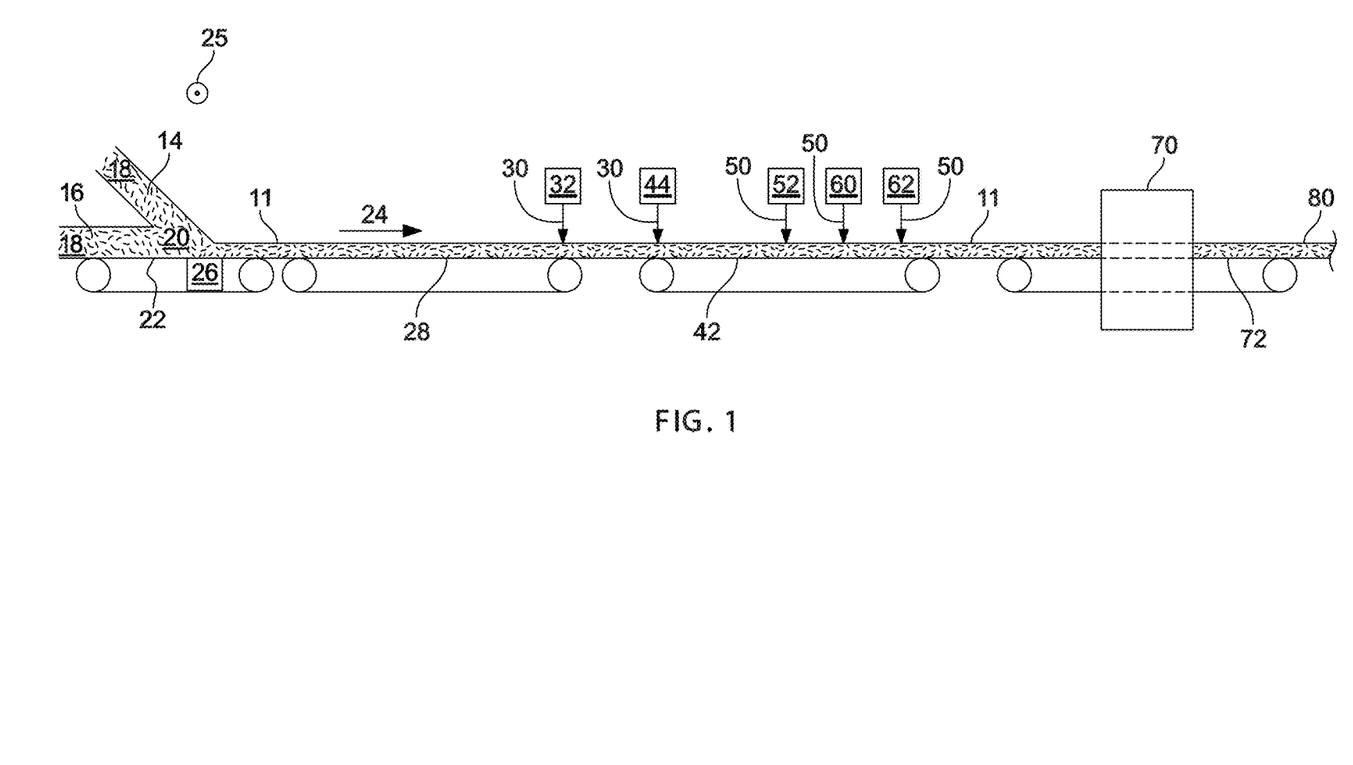
FIG. 1 is a schematic of one suitable embodiment of an apparatus for making dispersible moist wipes.

One suitable embodiment of an apparatus, indicated generally at 10, for making a dispersible nonwoven sheet 80 for making dispersible moist wipes is shown in FIG. 1. The apparatus 10 is configured to form a nonwoven fibrous web 11 comprising a mixture of natural cellulose fibers 14 and regenerated cellulose fibers 16. The natural cellulose fibers 14 are cellulosic fibers derived from woody or non-woody plants including, but not limited to, southern softwood kraft, northern softwood kraft, softwood sulfite pulp, cotton, cotton linters, bamboo, and the like. In some embodiments, the natural fibers 14 have a length-weighted average fiber length greater than about 1 millimeter. Furthermore, the natural fibers 14 may have a length-weighted average fiber length greater than about 2 millimeters. In other suitable embodiments, the natural fibers 14 are short fibers having a fiber length between about 0.5 millimeters and about 1.5 millimeters.

The regenerated fibers 16 are man-made filaments obtained by extruding or otherwise treating regenerated or modified cellulosic materials from woody or non-woody plants, as is known in the art. For example, but not by way of limitation, the regenerated fibers 16 may include one or more of lyocell, rayon, and the like. In some embodiments, the regenerated fibers 16 have a fiber length in the range of about 3 to about 20 millimeters. Furthermore, the regenerated fibers 16 may have a fiber length in the range of about 6 to about 12 millimeters. Additionally, in some embodiments, the regenerated fibers 16 may have a fineness in the range of about 1 to about 3 denier. Moreover, the fineness may be in the range of about 1.2 to about 2.2 denier.

In some other suitable embodiments, it is contemplated to use synthetic fibers in combination with, or as a substitute for, the regenerated fibers 16. For example, but not by way of limitation, the synthetic fibers may include one or more of nylon, polyethylene terephthalate (PET), and the like. In some embodiments, the synthetic fibers have a fiber length in the range of about 3 to about 20 millimeters. Furthermore, the synthetic fibers may have a fiber length in the range of about 6 to about 12 millimeters.

As illustrated in FIG. 1, the natural fibers 14 and regenerated fibers 16 are dispersed in a liquid suspension 20 to a headbox 12. A liquid medium 18 used to form the liquid suspension 20 may be any liquid medium known in the art that is compatible with the process as described herein, for example, water. In some embodiments, a consistency of the liquid suspension 20 is in the range of about 0.02 to about 0.08 percent fiber by weight. Moreover, the consistency of the liquid suspension 20 may be in the range of about 0.03 to about 0.05 percent fiber by weight. In one suitable embodiment, the consistency of the liquid suspension 20 after the natural fibers 14 and regenerated fibers 16 are added is about 0.03 percent fiber by weight. A relatively low consistency of the liquid suspension 20 at the headbox 12 is believed to enhance a mixing of the natural fibers 14 and regenerated fibers 16 and, therefore, enhances a formation quality of the nonwoven web 11.

In one suitable embodiment, of the total weight of fibers present in the liquid suspension 20, a ratio of natural fibers 14 and regenerated fibers 16 is about 80 to about 90 percent by weight natural fibers 14 and about 10 to about 20 percent by weight regenerated fibers 16. For example, of the total weight of fibers present in the liquid suspension 20, the natural fibers 14 may be 85 percent of the total weight and the regenerated fibers 16 may be 15 percent of the total weight.

The headbox 12 is configured to deposit the liquid suspension 20 onto a foraminous forming wire 22, which retains the fibers to form the nonwoven fibrous web 11. In an embodiment, the headbox 12 is configured to operate in a low-consistency mode as is described in U.S. Pat. No. 7,588,663, issued to Skoog et al. and assigned to Kimberly-Clark Worldwide, Inc., which is herein incorporated by reference. In another suitable embodiment, the headbox 12 is any headbox design that enables forming the nonwoven tissue web 11 such that it has a Formation Number of at least 18. The forming wire 22 carries the web 11 in a direction of travel 24. An axis of the nonwoven tissue web 11 aligned with the direction of travel 24 may hereinafter be referred to as "machine direction," and an axis in the same plane which is perpendicular to the machine direction may hereinafter be referred to as "cross-machine direction" 25. In some embodiments, the apparatus 10 is configured to draw a portion of the remaining liquid dispersing medium 18 out of the wet nonwoven tissue web 11 as the web 11 travels along the forming wire 22, such as by the operation of a vacuum box 26.

The apparatus 10 also may be configured to transfer the nonwoven tissue web 11 from the forming wire 22 to a transfer wire 28. In some embodiments, the transfer wire 28 carries the nonwoven web in the machine direction 24 under a first plurality of jets 30. The first plurality of jets 30 may be produced by a first manifold 32 with at least one row of first orifices 34 spaced apart along the cross-machine direction 25. The first manifold 32 is configured to supply a liquid, such as water, at a first pressure to the first orifices 34 to produce a columnar jet 30 at each first orifice 34. In some embodiments, the first pressure is in the range of about 20 to about 125 bars. In one suitable embodiment, the first pressure is about 35 bars.

In some embodiments, each first orifice 34 is of circular shape with a diameter in the range of about 90 to about 150 micrometers. In one suitable embodiment, for example, each first orifice 34 has a diameter of about 120 micrometers. In addition, each first orifice 34 is spaced apart from an adjacent first orifice 34 by a first distance 36 along the cross-machine direction 25. Contrary to what is known in the art, in some embodiments the first distance 36 is such that a first region 38 of fibers of the nonwoven tissue web 11 displaced by each jet of the first plurality of jets 30 does not overlap substantially with a second region 40 of fibers displaced by the adjacent one of the first plurality of jets 30, as illustrated schematically in FIG. 2. Instead, the fibers in each of the first region 38 and the second region 40 are substantially displaced in a direction along an axis 46 perpendicular to the plane of nonwoven web 11, but are not significantly hydroentangled with laterally adjacent fibers. In some embodiments, the first distance 36 is in the range of about 1200 to about 2400 micrometers. In an embodiment, the first distance 36 is about 1800 micrometers. In alternative embodiments, the first plurality of jets 30 may be produced by first orifices 34 having any shape, or any jet nozzle and pressurization arrangement, that is configured to produce a row of columnar jets 30 spaced apart along the cross-machine direction 25 in like fashion.

Additional ones of the first plurality of jets 30 optionally may be produced by additional manifolds, such as a second manifold 44 shown in the exemplary embodiment of FIG. 1, spaced apart from the first manifold 32 in the direction of machine travel. A foraminous support fabric 42 is configured such that the nonwoven tissue web 11 may be transferred from the transfer wire 28 to the support fabric 42. In an embodiment, the support fabric 42 carries the nonwoven tissue web 11 in the machine direction 24 under the second manifold 44. It should be understood that the number and placement of transport wires or transport fabrics, such as the forming wire 22, the transport wire 28, and the support fabric 42, may be varied in other embodiments. For example, but not by way of limitation, the first manifold 32 may be located to treat the nonwoven tissue web 11 while it is carried on the support fabric 42, rather than on the transfer wire 28, or conversely the second manifold 44 may be located to treat the nonwoven tissue web 11 while it is carried on the transfer wire 28, rather than on the support fabric 42. For another example, one of the forming wire 22, the transport wire 28, and the support fabric 42 may be combined with another in a single wire or fabric, or any one may be implemented as a series of cooperating wires and transport fabrics rather than as a single wire or transport fabric.

Figure 2:
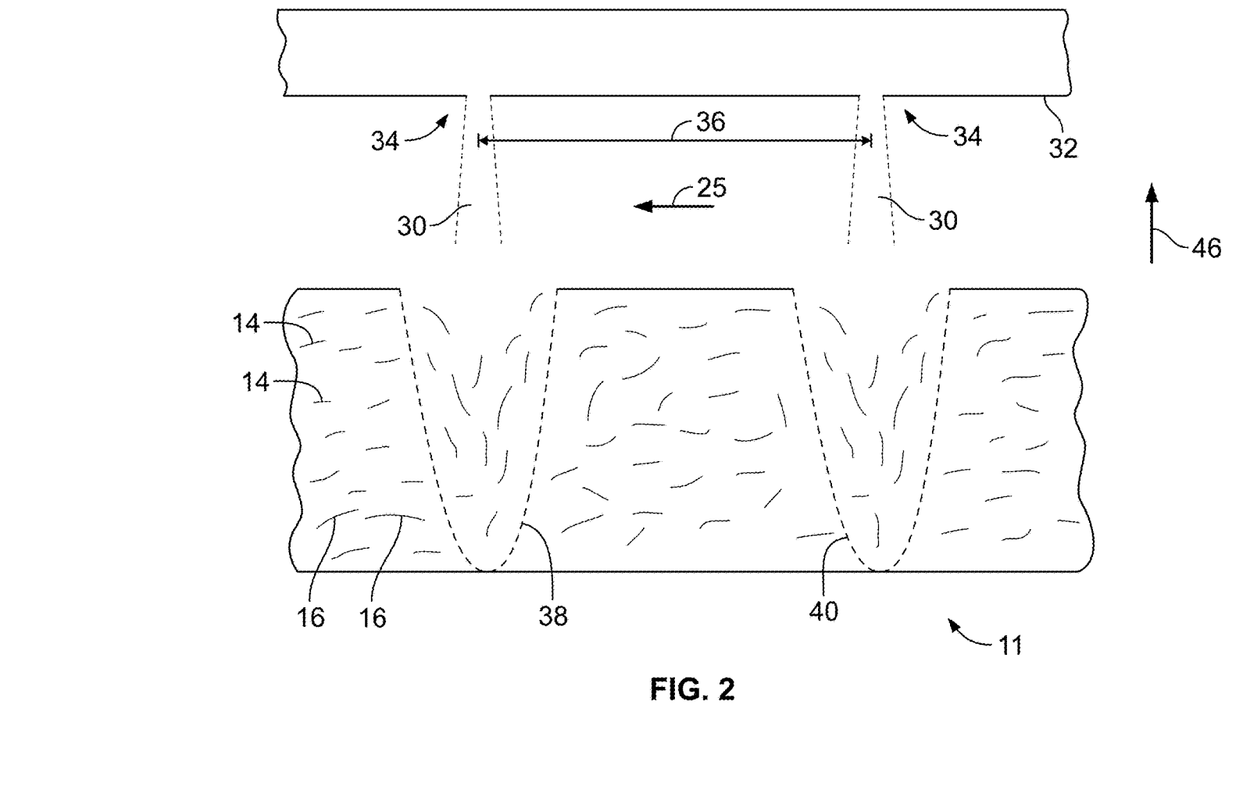
FIG. 2 is a schematic of a nonwoven web at one location within the apparatus of FIG. 1.

In some embodiments, the second manifold 44, like the first manifold 32, includes at least one row of first orifices 34 spaced apart along the cross-machine direction 25. The second manifold 44 is configured to supply a liquid, such as water, at a second pressure to the first orifices 34 to produce a columnar jet 30 at each first orifice 34. In some embodiments, the second pressure is in the range of about 20 to about 125 bars. In an embodiment, the second pressure is about 75 bars. Moreover, in some embodiments, each first orifice 34 is of circular shape, and each first orifice 34 is spaced apart from an adjacent first orifice 34 by a first distance 36 along the cross-machine direction 25, as shown in FIG. 2 for the first manifold 32. In alternative embodiments, the second manifold 44 may be configured in any other fashion such that a first region of fibers of nonwoven tissue web 11 displaced by each jet of the first plurality of jets 30 does not overlap substantially with a second region of fibers displaced by the adjacent one of the first plurality of jets 30.

With reference again to FIG. 1, the support fabric 42 carries the nonwoven web 11 in the machine direction 24 under a second plurality of jets 50. The second plurality of jets 50 may be produced by a third manifold 52 with at least one row of second orifices 54 spaced apart along the cross-machine direction 25. The third manifold 52 is configured to supply a liquid, such as water, at a third pressure to the second orifices 54 to produce a columnar jet 50 at each third orifice 54. In some embodiments, the third pressure is in the range of about 20 to about 120 bars. Further, the third pressure may be in the range of about 40 to about 90 bars.

Figure 3:
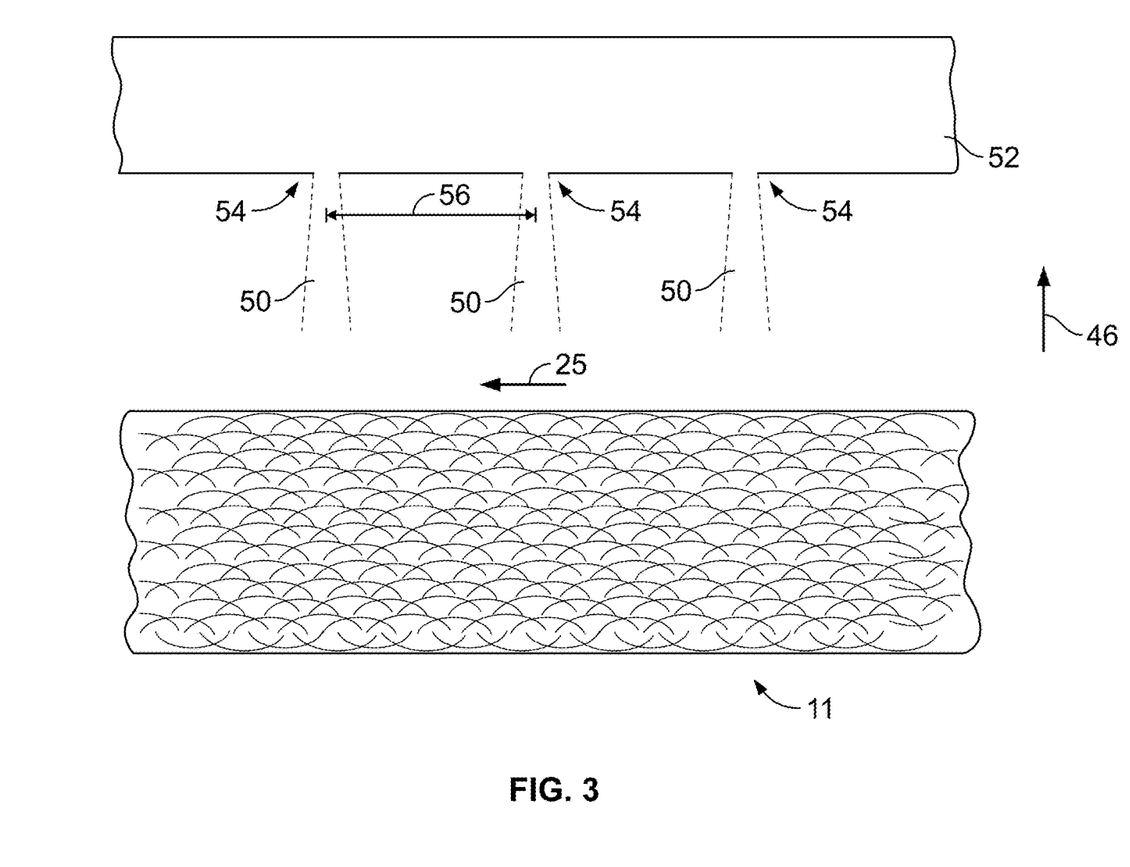
FIG. 3 is a schematic of a nonwoven web at another location within the apparatus of FIG. 1.

In some embodiments, each second orifice 54 is of circular shape with a diameter in the range of about 90 to about 150 micrometers. Moreover, each second orifice 54 may have a diameter of about 120 micrometers. In addition, each second orifice 54 is spaced apart from an adjacent second orifice 54 by a second distance 56 along the cross-machine direction 25, as illustrated in FIG. 3, and the second distance 56 is such that the fibers of the nonwoven tissue web 11 become substantially hydroentangled. In some embodiments, the second distance 56 is in the range of about 400 to about 1000 micrometers. Further, the second distance 56 may be in the range of about 500 to about 700 micrometers. In an embodiment, the second distance 56 is about 600 micrometers. In alternative embodiments, the second plurality of jets 50 may be produced by second orifices 54 having any shape, or any jet nozzle and pressurization arrangement, that is configured to produce a row of columnar jets 50 spaced apart along the cross-machine direction 25 in like fashion.

Additional ones of the second plurality of jets 50 optionally may be produced by additional manifolds, such as a fourth manifold 60 and a fifth manifold 62 shown in the exemplary embodiment of FIG. 1. Each of the fourth manifold 60 and the fifth manifold 62 have at least one row of second orifices 54 spaced apart along the cross-machine direction 25. In an embodiment, the fourth manifold 60 and the fifth manifold 62 each are configured to supply a liquid, such as water, at the third pressure (that is, the pressure at third manifold 52) to the second orifices 54 to produce a columnar jet 50 at each third orifice 54. In alternative embodiments, each of the fourth manifold 60 and the fifth manifold 62 may supply the liquid at a pressure other than the third pressure. Moreover, in some embodiments, each second orifice 54 is of circular shape with a diameter in the range of about 90 to about 150 micrometers, and each second orifice 54 is spaced apart from an adjacent second orifice 54 by a second distance 56 along the cross-machine direction 25, as with third manifold 52. In alternative embodiments, the fourth manifold 60 and the fifth manifold 62 each may be configured in any other fashion such as to produce jets 50 that cause the fibers of nonwoven tissue web 11 to become substantially hydroentangled.

It should be recognized that, although the embodiment shown in FIG. 1 has two pre-entangling manifolds and three hydroentangling manifolds, any number of additional pre-entangling manifolds and/or hydroentangling manifolds may be used. In particular, each of the forming wire 22, the transfer wire 28, and the support fabric 42 carry the nonwoven tissue web 11 in the direction of machine travel at a respective speed, and as those respective speeds are increased, additional manifolds may be necessary to impart a desired hydroentangling energy to the nonwoven web 11.

The apparatus 10 also may be configured to remove a desired portion of the remaining fluid, for example water, from the nonwoven tissue web 11 after the hydroentanglement process to produce a dispersible nonwoven sheet 80. In some embodiments, the hydroentangled nonwoven web 11 is transferred from the support fabric 42 to a through-drying fabric 72, which carries the nonwoven web 11 through a through-air dryer 70. In some embodiments, the through-drying fabric 72 is a coarse, highly permeable fabric. The through-air dryer 70 is configured to pass hot air through the nonwoven tissue web 11 to remove a desired amount of fluid. Thus, the through-air dryer 70 provides a relatively non-compressive method of drying the nonwoven tissue web 11 to produce the dispersible nonwoven sheet 80. In alternative embodiments, other methods may be used as a substitute for, or in conjunction with, the through-air dryer 70 to remove a desired amount of remaining fluid from the nonwoven tissue web 11 to form the dispersible nonwoven sheet 80. Furthermore, in some suitable embodiments, the dispersible nonwoven sheet 80 may be wound on a reel (not shown) to facilitate storage and/or transport prior to further processing. The dispersible nonwoven sheet 80 may then be processed as desired, for example, infused with a wetting composition including any combination of water, emollients, surfactants, fragrances, preservatives, organic or inorganic acids, chelating agents, pH buffers, and the like, and cut, folded and packaged as a dispersible moist wipe.

Figure 7:
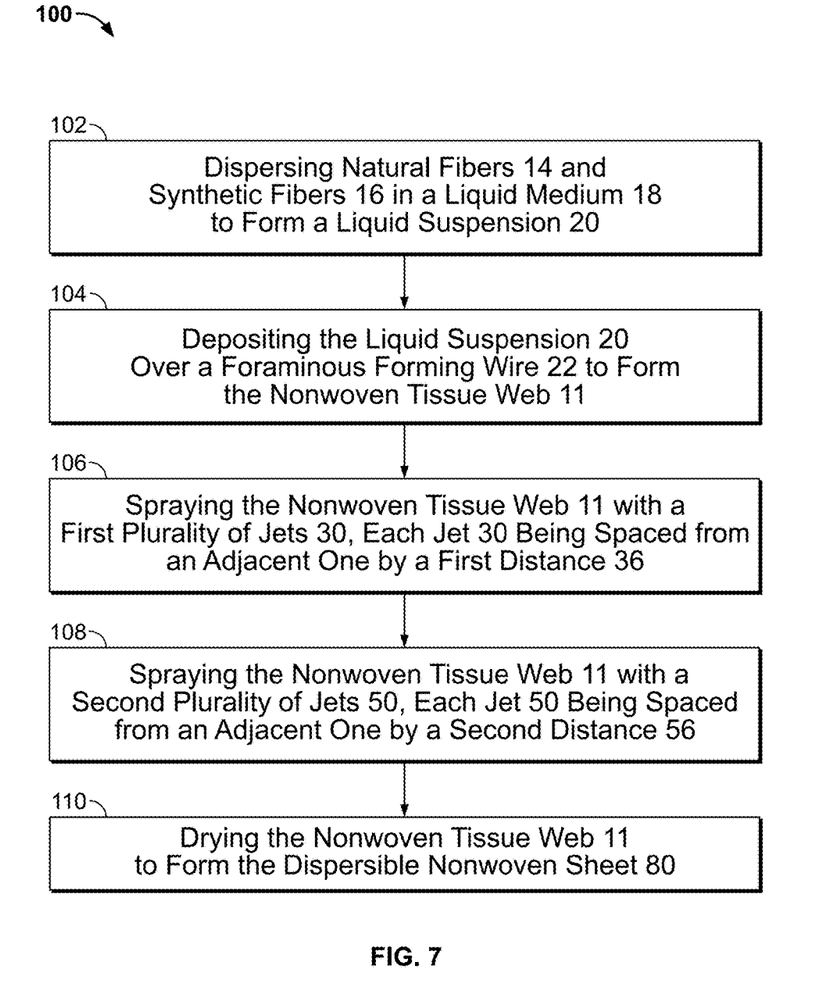
FIG. 7 is a flow chart of an embodiment of a process for making a moist dispersible wipe.

A method 100 for making a dispersible nonwoven sheet 80 is illustrated in FIG. 7. The method 100 includes dispersing 102 natural fibers 14 and regenerated fibers 16 in a ratio of about 80 to about 90 percent by weight natural fibers 14 and about 10 to about 20 percent by weight regenerated fibers 16 in a liquid medium 18 to form a liquid suspension 20. It also includes 104 depositing the liquid suspension 20 over a foraminous forming wire 22 to form the nonwoven tissue web 11. The method 100 further includes spraying 106 the nonwoven tissue web 11 with a first plurality of jets 30, each jet 30 being spaced from an adjacent one by a first distance 36. Additionally, the method 100 includes spraying 108 the nonwoven tissue web 11 with a second plurality of jets 50, each jet 50 being spaced from an adjacent one by a second distance 56, wherein the second distance 56 is less than the first distance 36. The method 100 moreover includes drying 110 the nonwoven tissue web 11 to form the dispersible nonwoven sheet 80.

Figure 4:
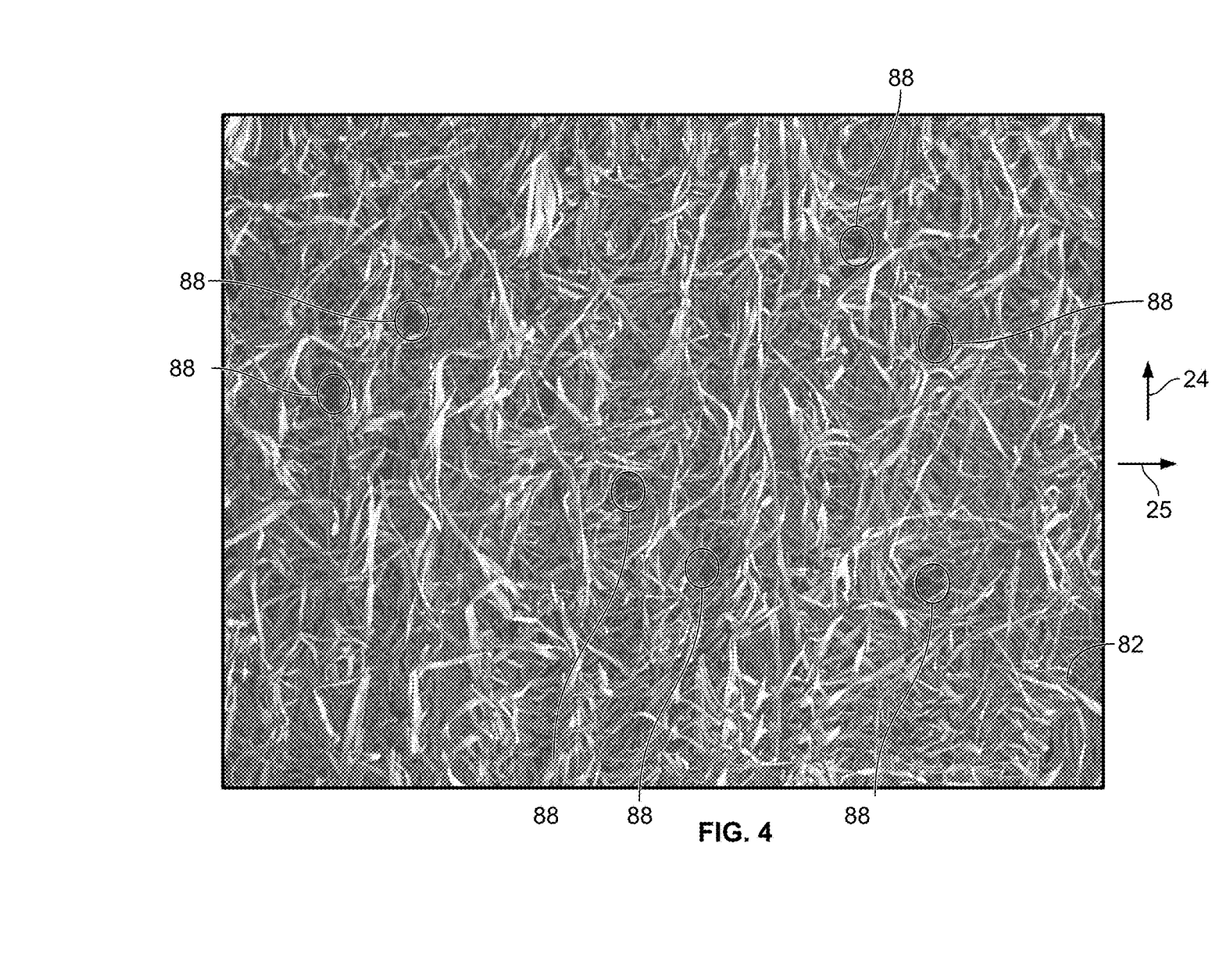
FIG. 4 is a bottom view of one suitable embodiment of a nonwoven web.
Figure 5:
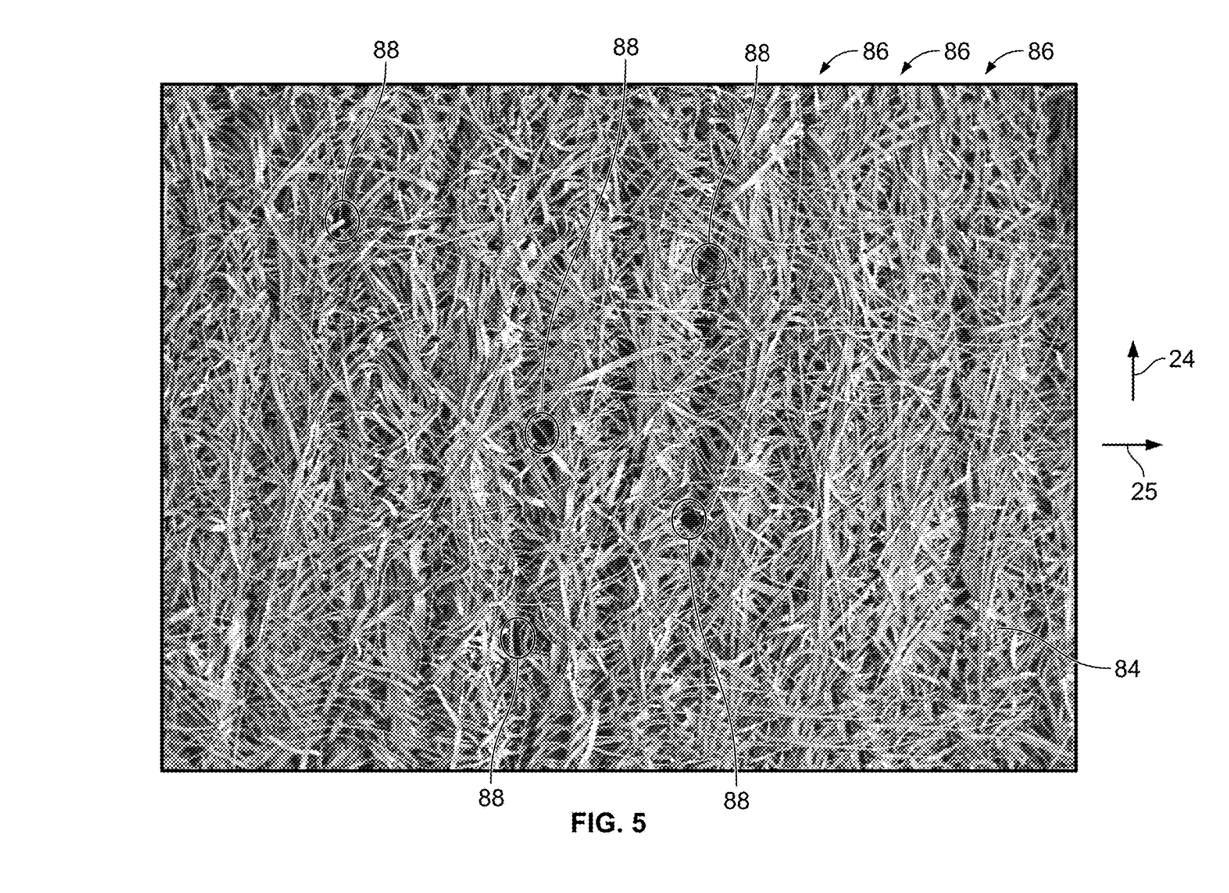
FIG. 5 is a top view of one suitable embodiment of a nonwoven web.
Figure 6:
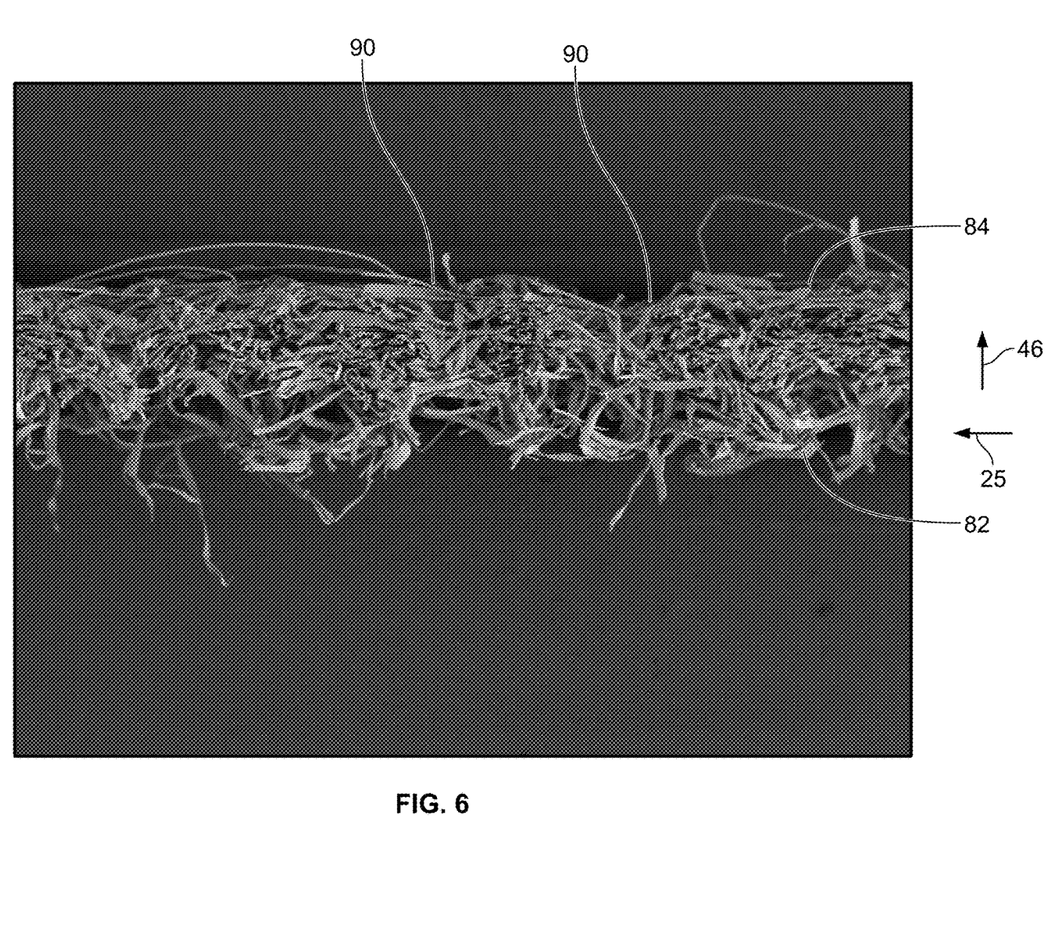
FIG. 6 is a side view of one suitable embodiment of a nonwoven web.

One suitable embodiment of the nonwoven sheet 80 made using the method described above is illustrated in FIG. 4, FIG. 5, and FIG. 6. An enlarged view of a bottom side 82, that is, the side in contact during manufacture with the forming wire 22, the transfer wire 28, and the support fabric 42, of a portion of the nonwoven sheet 80 is shown in FIG. 4. An enlarged view of a top side 84, that is, the side opposite the bottom side 82, of a portion of the nonwoven sheet 80 is shown in FIG. 5. The portion shown in each figure measures approximately 7 millimeters in the cross machine direction 25. As best seen in FIG. 5, the nonwoven sheet 80 includes ribbon-like structures 86 of relatively higher entanglement along the machine direction 24, each ribbon-like structure 86 is spaced apart in the cross-machine direction 25 at a distance approximately equal to the second distance 56 between second orifices 54 of the second plurality of jets 50. In addition, at some locations between the ribbon-like structures 86, holes 88 are visible, as seen in FIG. 4 and FIG. 5. The holes 88 often are more pronounced in the bottom surface 82 due to the high-impact of the jets 30 and 50 against the transfer wire 28 adjacent the bottom surface 82 during the hydroentangling process. As visible in a side view of a portion of the nonwoven sheet 80 in FIG. 6, certain areas 90 of the nonwoven sheet 80 display less fiber entanglement through a thickness of the sheet 80, and more displacement in the direction 46 perpendicular to the plane of the sheet 80. The more pronounced areas 90 may appear as holes 88 when viewed from the top or bottom.

EXAMPLES

A series of example dispersible nonwoven sheets 80 was prepared as described below. For all of the examples, southern softwood kraft was selected as the natural fibers 14 and TENCEL® brand lyocell with a fineness of 1.7 deniers was selected as the regenerated fibers 16. The nominal length of the regenerated fibers 16 used in each example is set forth in column 2 of Table 1, and the percent total fiber of regenerated fibers 16 and natural fibers 14 is set forth in columns 3 and 4. The nominal basis weight of each sheet was 65 grams per meter squared.

For all of the examples, the first plurality of jets 30 was provided by first and second manifolds and the second plurality of jets 50 was provided by third, fourth and fifth manifolds. The support fabric rate of travel was 30 meters per minute. For all of the examples, the first manifold pressure was 35 bars, the second manifold pressure was 75 bars, the first and second manifolds both had 120 micrometer orifices spaced 1800 micrometers apart in the cross-machine direction, and the third, fourth and fifth manifolds each had 120 micrometer orifices spaced 600 micrometers apart in the cross-machine direction. The third, fourth and fifth manifolds each operated at the same pressure for a given example, and that pressure is set forth in column 5 of Table 1. The hydroentangling energy E in kilowatt-hours per kilogram imparted to the web is set forth in column 6, as calculated by the summing the energy over each of the injectors (i):

$$E = 0.278 \sum_i \frac{Q_i P_i}{M_r}$$

where $P_i$ is the pressure in Pascals for injector i, $M_r$ is the mass of sheet passing under the injector per second in kilograms per second (calculated by multiplying the basis weight of the sheet by the web velocity), and $Q_i$ is the volume flow rate out of injector i in cubic meters per second, calculated according to:

$$Q_i = N_i \frac{0.8 D_i^2 \pi}{4} \sqrt{\frac{2 P_i}{\rho}}$$

where $N_i$ is the number of nozzles per meter width of injector i, $D_i$ is the nozzle diameter in meters, $\rho$ is the density of the hydroentangling water in kilograms per cubic meter, and 0.8 is used as the nozzle coefficient for all nozzles.

TABLE 1

| Example | Regenerated Fiber Length (mm) | % Regenerated Fiber | % Natural Fiber | Pressure (manifolds 3-5) (bar) | Energy (kW-h/kg) |
|---|---|---|---|---|---|
| 1 | 12 | 20 | 80 | 20 | 0.120 |
| 2 | 12 | 20 | 80 | 20 | 0.120 |
| 3 | 12 | 20 | 80 | 40 | 0.227 |
| 4 | 12 | 20 | 80 | 60 | 0.365 |
| 5 | 12 | 20 | 80 | 60 | 0.365 |
| 6 | 12 | 20 | 80 | 80 | 0.529 |
| 7 | 12 | 20 | 80 | 80 | 0.529 |
| 8 | 12 | 20 | 80 | 100 | 0.714 |
| 9 | 12 | 20 | 80 | 120 | 0.920 |
| 10 | 6 | 20 | 80 | 75 | 0.336 |
| 11 | 6 | 20 | 80 | 90 | 0.495 |
| 12 | 12 | 10 | 90 | 20 | 0.120 |
| 13 | 12 | 10 | 90 | 40 | 0.227 |
| 14 | 12 | 10 | 90 | 60 | 0.365 |
| 15 | 12 | 10 | 90 | 80 | 0.529 |

The strength of the dispersible nonwoven sheets 80 generated from each example was evaluated by measuring the tensile strength in the machine direction 24 and the cross-machine direction 25. Tensile strength was measured using a Constant Rate of Elongation (CRE) tensile tester having a 1-inch jaw width (sample width), a test span of 3 inches (gauge length), and a rate of jaw separation of 25.4 centimeters per minute after soaking the sheet in tap water for 4 minutes and then draining the sheet on dry Viva® brand paper towel for 20 seconds. This drainage procedure resulted in a moisture content of 200 percent of the dry weight+/−50 percent. This was verified by weighing the sample before each test. One-inch wide strips were cut from the center of the dispersible nonwoven sheets 80 in the specified machine direction 24 ("MD") or cross-machine direction 25 ("CD") orientation using a JDC Precision Sample Cutter (Thwing-Albert Instrument Company, Philadelphia, Pa., Model No. JDC3-10, Serial No. 37333). The "MD tensile strength" is the peak load in grams-force per inch of sample width when a sample is pulled to rupture in the machine direction. The "CD tensile strength" is the peak load in grams-force per inch of sample width when a sample is pulled to rupture in the cross direction.

The instrument used for measuring tensile strength was an MTS Systems Sinergie 200 model and the data acquisition software was MTS TestWorks® for Windows Ver. 4.0 commercially available from MTS Systems Corp., Eden Prairie, Minn. The load cell was an MTS 50 Newton maximum load cell. The gauge length between jaws was 4±0.04 inches and the top and bottom jaws were operated using pneumatic-action with maximum 60 P.S.I. The break sensitivity was set at 70 percent. The data acquisition rate was set at 100 Hz (i.e., 100 samples per second). The sample was placed in the jaws of the instrument, centered both vertically and horizontally. The test was then started and ended when the force drops by 70 percent of peak. The peak load was expressed in grams-force and was recorded as the "MD tensile strength" of the specimen. At least twelve representative specimens were tested for each product and the average peak load was determined. As used herein, the "geometric mean tensile strength" ("GMT") is the square root of the product of the wet machine direction tensile strength multiplied by the wet cross-machine direction tensile strength and is expressed as grams per inch of sample width. All of these values are for in-use tensile strength measurements. Generally, a GMT of 550 grams-force per inch or greater is considered very good, and a strength of at least 250 grams-force per inch is considered to be the minimum acceptable value for consumer use.

The dispersibility of the dispersible nonwoven sheets 80 was measured in two ways: 1) using the INDA/EDANA Guidance Document for Assessing the Flushability of Nonwoven Consumer Products, Dispersibilty Shake Flask Test, and 2) using a slosh box test.

The Dispersibilty Shake Flask Test is used to assess the dispersibility or physical breakup of a flushable product during its transport through sewage pumps (e.g., ejector or grinder pumps) and municipal wastewater conveyance systems (e.g., sewer pipes and lift stations). This test assesses the rate and extent of disintegration of a test material in the presence of tap water or raw wastewater. Results from this test are used to predict the compatibility of a flushable product with household sewage pumps and municipal collection systems. The materials and apparatus used to conduct the Dispersibilty Shake Flask Test on the examples were:

1. Fernbach triple-baffled, glass, culture flasks (2800 mL).
2. Orbital floor shaker with 2-in (5-cm) orbit capable of 150 rpm. The platform for the shaker needs clamps to be able to accommodate a bottom flask diameter of 205 mm.
3. USA Standard Testing Sieve #18 (1 mm opening): 8 in (20 cm) diameter.
4. Perforated Plate Screens details

| Hole Size (mm) | Hole size (in) | Hole Center | Pattern | Gauge | % open area |
|---|---|---|---|---|---|
| 12.75 mm | ½" | ¹¹⁄₁₆" | Staggered | 16 SWG | 48% |
| 6.35 mm | ¼" | ⁵⁄₁₆" | Staggered | 16 SWG | 58% |
| 3.18 mm | ⅛" | ³⁄₁₆" | Staggered | 20 SWG | 40% |
| 1.59 mm | ¹⁄₁₆" | ³⁄₃₂" | Staggered | 20 SWG | 41% |

5. Drying oven capable of maintaining a temperature of 40±3° C. for thermoplastic test materials and capable of maintaining a temperature of 103±3° C. for non-plastic test materials.

Each test product was run in triplicate. As a result, three flasks were prepared for each of the two predetermined destructive sampling time points. Each flask contained one liter of room temperature tap water. Each test product was pre-weighed in triplicate (dry weight basis) on an analytical balance that measures at least 2-decimal places and then the weights were recorded in a laboratory notebook for later use in the final percent disintegration calculations. Control flasks with the reference material were also run to accommodate two destructive sampling time points. Each control flask also contained one liter of tap water and the appropriate reference material.

One liter of tap water was measured and placed into each of the Fernbach flasks and the flasks were then placed on the rotary shaker table. The test example was added to the flasks. The flasks were then shaken at 150 rpm, observed after 30 and 60 minutes, and then destructively sampled at three hours. At the designated destructive sampling point of three hours, a flask from each set of products being tested and the control set was removed and the contents poured through a nest of screens arranged from top to bottom in the following order: 12 mm, 6 mm, 3 mm and 1.5 mm (diameter opening). With a hand held showerhead spray nozzle held approximately 10 to 15 cm above the sieve, the material was gently rinsed through the nested screens for two minutes at a flow rate of 4 L/min being careful not to force passage of the retained material through the next smaller screen. After two minutes of rinsing, the top screen was removed and rinsing of the next smaller screen, still nested, continued for two additional minutes using the same procedure as above. The rinsing process was continued until all of the screens had been rinsed. After rinsing was complete, the retained material was removed from each of the screens using forceps into a smaller sized sieve. The content from each screen was transferred to a separate, labeled tared aluminum weigh pan and dried overnight at 103±3° C. The dried samples were then cooled in a desiccator. After cooling, the material collect from each of the sieves was weighed and the percentage of disintegration based on the initial starting weight of the test material was calculated. Generally, a Pass Through Percentage Value of 80 percent or greater at the 12 mm screen is considered very good, and a Pass Through Percentage Value of at least 25 percent at the 12 mm screen is considered to be the minimum acceptable value for flushability.

The Slosh Box Test uses a bench-scaled apparatus to evaluate the breakup or dispersibility of flushable consumer products as they travel through the wastewater collection system. In this test, a clear plastic tank was loaded with a product and tap water or raw wastewater. The container was then moved up and down by a cam system at a specified rotational speed to simulate the movement of wastewater in the collection system. The initial breakup point and the time for dispersion of the product into pieces measuring 1 inch by 1 inch (25 mm by 25 mm) were recorded in the laboratory notebook. This 1 inch by 1 inch (25 mm by 25 mm) size is a parameter that is used because it reduces the potential of product recognition. The various components of the product were then screened and weighed to determine the rate and level of disintegration.

The slosh box water transport simulator consisted of a transparent plastic tank that was mounted on an oscillating platform with speed and holding time controller. The angle of incline produced by the cam system produces a water motion equivalent to 60 cm/s (2 ft/s), which is the minimum design standard for wastewater flow rate in an enclosed collection system. The rate of oscillation was controlled mechanically by the rotation of a cam and level system and was measured periodically throughout the test. This cycle mimics the normal back-and forth movement of wastewater as it flows through sewer pipe.

Room temperature tap water was placed in the plastic container/tank. The timer was set for six hours (or longer) and cycle speed is set for 26 rpm. The pre-weighed product was placed in the tank and observed as it underwent the agitation period. The time to first breakup and full dispersion were recorded in the laboratory notebook.

The test was terminated when the product reached a dispersion point of no piece larger than 1 inch by 1 inch (25 mm by 25 mm) square in size. At this point, the clear plastic tank was removed from the oscillating platform. The entire contents of the plastic tank were then poured through a nest of screens arranged from top to bottom in the following order: 25.40 mm, 12.70 mm, 6.35 mm, 3.18 mm, 1.59 mm (diameter opening). With a showerhead spray nozzle held approximately 10 to 15 cm (4 to 6 in) above the sieve, the with 1000 being completely uniform. The C9 PPF values reported for each sample were based on the average of ten tests on five samples (two tests per sample).

The results of testing samples from each example for strength are shown in Table 2. In addition, samples from Examples 2, 3, 6, 9, 11, 12 and 15 were subjected to the Shaker Flask and Slosh Box dispersibility tests, and those results are reported in Table 2 as well. Finally, samples from Examples 3, 4, 9, 10 and 15 were tested for Formation Value, and those results are reported in the final column of Table 2.

TABLE 2

| Example | MDT (gf/in) | CDT (gf/in) | GMT (gf/in) | Shaker Flask (% Pass Through, 12 mm screen) | Shaker Flask (% Pass Through, 6 mm screen) | Slosh Box (minutes until all pieces smaller than 25 mm by 25 mm) | Formation Value |
|---|---|---|---|---|---|---|---|
| 1 | 404 | 151 | 247 | — | — | — | — |
| 2 | 333 | 163 | 233 | 77 | 52 | 4.25 | — |
| 3 | 632 | 229 | 381 | 67 | 50 | 23.8 | 23.1 |
| 4 | 899 | 360 | 569 | — | — | — | 13.3 |
| 5 | 956 | 318 | 551 | — | — | — | — |
| 6 | 1291 | 539 | 834 | 30 | 24 | >180 | — |
| 7 | 1347 | 486 | 809 | — | — | — | — |
| 8 | 1588 | 517 | 906 | — | — | — | — |
| 9 | 1929 | 592 | 1068 | 9 | 9 | >180 | 22 |
| 10 | 461 | 189 | 295 | — | — | — | 20.1 |
| 11 | 496 | 213 | 325 | 81 | 43 | 152 | — |
| 12 | 242 | 104 | 158 | 96 | 71 | 7.75 | — |
| 13 | 312 | 127 | 199 | — | — | — | — |
| 14 | 492 | 164 | 284 | — | — | — | — |
| 15 | 660 | 220 | 381 | 81 | 55 | 81.4 | 16.6 | material was gently rinsed through the nested screens for two minutes at a flow rate of 4 L/min (1 gal/min) being careful not to force passage of the retained material through the next smaller screen. After two minutes of rinsing, the top screen was removed and the rinsing continued for the next smaller screen, still nested, for two additional minutes. After rinsing was complete, the retained material was removed from each of the screens using forceps. The contents were transferred from each screen to a separate, labeled aluminum weigh pan. The pan was placed in a drying oven overnight at 103±3° C. The dried samples were allowed to cool down in a desiccator. After all the samples were dry, the materials from each of the retained fractions were weighed and the percentage of disintegration based on the initial starting weight of the test material were calculated. Generally, a Slosh Box break-up time into pieces less than 25 mm by 25 mm of 100 minutes or less is considered very good, and a Slosh Box break-up time into pieces less than 25 mm by 25 mm of 180 minutes is considered to be the maximum acceptable value for flushability.

Finally, the formation value of the dispersible nonwoven sheets 80 was tested using the Paper PerFect Formation Analyzer Code LPA07 from OPTEST Equipment Inc. (OpTest Equipment Inc. 900 Tupper St., Hawkesbury, ON, Canada). The samples were tested using the procedure outlined in Section 10.0 of the Paper PerFect Code LPA07 Operation Manual (LPA07_PPF_Operation_Manual_004. wpd 2009-05-20). The formation analyzer gives PPF formation values calculated for ten size ranges from C1 for 0.5 to 0.7 mm to C10 for 31 to 60 mm. The smaller sizes are important for printing clarity and the larger sizes are important for strength properties. For purposes herein, the C9 PPF value for the formation size range from 18.5 to 31 mm was used to generate a measurement for the strength of the examples. The PPF values are based on a 1000 point scale Unexpectedly, it was discovered that the dispersible nonwoven sheets 80 created at relatively very high hydroentangling energies, up to more than 0.9 kW-h/kg, continued to develop additional strength, such as a machine direction tensile strength of 1,929 grams-force per inch for Example 9. Also unexpectedly, it was discovered that the dispersible nonwoven sheets 80 still displayed acceptable dispersibility at relatively high hydroentangling energies, up to about 0.5 kW-h/kg. For example, the nonwoven sheets 80 from Example 11 dispersed into pieces of a size less than 25 mm by 25 mm in 150 minutes in the slosh box, and had an 81 percent pass-through rate at the 12 mm screen in the shaker flask.

Moreover, at relatively lower hydroentangling energies, unexpectedly good combinations of strength and dispersibility were achieved. For example, the nonwoven sheets 80 from Example 3 dispersed into pieces of a size less than 25 mm by 25 mm in less than 24 minutes in the slosh box, had a 67 percent pass-through rate at the 12 mm screen in the shaker flask, and displayed good geometric mean tensile strength of 381 grams-force per inch. For another example, the nonwoven sheets 80 from Example 15 dispersed into pieces of a size less than 25 mm by 25 mm in less than 82 minutes in the slosh box, had an 81 percent pass-through rate at the 12 mm screen in the shaker flask, and displayed good geometric mean tensile strength of 381 grams-force per inch.

Although the inventors do not wish herein to be held to any theory, it is believed that in some embodiments, the tendency of relatively widely spaced first plurality of jets 30 to displace fibers substantially in a direction along axis 46 perpendicular to the plane of nonwoven web 11, but not to cause significant hydroentanglement with laterally adjacent fibers, serves to prepare the nonwoven web 11 for more effective hydroentanglement from the relatively closely spaced second plurality of jets 50, resulting in better strength at a given hydroentangling energy. In addition, the good formation afforded by the use of the low consistency former allows for more effective hydroentangling of single fibers rather than clumps or nits of fibers. Moreover, because the unexpected strength is achieved without the use of a non-dispersible net or thermoplastic binder, in some embodiments the dispersibility of the nonwoven sheets 80 remains relatively high. An added benefit in some embodiments is the use of about 80 to about 90 percent natural fibers 14, and therefore only about 10 to about 20 percent of the more expensive regenerated fibers 16, reducing a cost associated with dispersible nonwoven sheet 80.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dispersible moist wipe comprising a nonwoven tissue web having regenerated fibers in an amount of about 10 to about 30 percent by weight and natural fibers in an amount of about 70 to about 90 percent by weight, wherein the regenerated fibers and the natural fibers are hydroentangled using an energy within a range between about 0.12 kw-hr/kg and about 0.9 kw-hr/kg such that the web has a geometric mean tensile strength of at least 150 grams per inch and a slosh-box break-up time of less than 155 minutes, the nonwoven tissue web being free of a binder and having a formation value of at least 12, wherein the nonwoven tissue web has at least one ribbon-like structure extending along the nonwoven tissue web, and at least one hole in the nonwoven tissue web positioned adjacent the at least one ribbon-like structure, the at least one ribbon-like structure defining an area of higher entanglement of the regenerated fibers and the natural fibers than in other areas of the nonwoven tissue web.

2. The dispersible moist wipe set forth in claim 1 wherein the web has a geometric mean tensile strength of at least 200 grams per inch and a slosh-box break-up time of less than 90 minutes.

3. The dispersible moist wipe set forth in claim 1 wherein the web has a geometric mean tensile strength of at least 250 grams per inch and a slosh-box break-up time of less than 30 minutes.

4. The dispersible moist wipe set forth in claim 1 wherein the nonwoven tissue web has a basis weight in the range of about 30 to about 90 grams per square meter.

5. The dispersible moist wipe set forth in claim 4 wherein the nonwoven tissue web has a basis weight in the range of about 60 to about 75 grams per square meter.

6. The dispersible moist wipe set forth in claim 1 wherein the regenerated fibers comprise at least one of lyocell fibers and rayon fibers.

7. The dispersible moist wipe set forth in claim 1 wherein the natural fibers comprise at least one of southern softwood kraft and cotton.

8. The dispersible moist wipe set forth in claim 1 wherein the regenerated fibers have a length in the range of about 4 millimeters to about 15 millimeters.

9. The dispersible moist wipe set forth in claim 8 wherein the regenerated fibers have a length in the range of about 6 millimeters to about 12 millimeters.

10. The dispersible moist wipe set forth in claim 1 wherein the regenerated fibers have a fineness in the range of about 1 to about 3 deniers.

11. The dispersible moist wipe set forth in claim 1 wherein the web has a formation value of at least 16.

12. A dispersible moist wipe comprising a nonwoven tissue web having regenerated fibers in an amount of about 10 to about 30 percent by weight and natural fibers in an amount of about 70 to about 90 percent by weight, wherein the regenerated fibers and the natural fibers are hydroentangled using an energy within a range between about 0.12 kw-hr/kg and about 0.9 kw-hr/kg such that the web has a geometric mean tensile strength of at least 150 grams per inch and a shaker flask pass-through percentage value at a 12 millimeter screen of at least 60 percent, the nonwoven tissue web being free of a binder and having a formation value of at least 12, wherein the nonwoven tissue web has at least one ribbon-like structure extending along the nonwoven tissue web, and at least one hole in the nonwoven tissue web positioned adjacent the at least one ribbon-like structure, the at least one ribbon-like structure defining an area of higher entanglement of the regenerated fibers and the natural fibers than in other areas of the nonwoven tissue web.

13. The dispersible moist wipe set forth in claim 12 wherein the web has a geometric mean tensile strength of at least 200 grams per inch.

14. The dispersible moist wipe set forth in claim 12 wherein the web has a shaker flask pass-through percentage value at a 12 millimeter screen of at least 80 percent.

15. The dispersible moist wipe set forth in claim 12 wherein the web has a ratio of machine direction tensile strength to cross direction tensile strength of less than about 4.

16. The dispersible moist wipe set forth in claim 12 wherein the regenerated fibers have a length in the range of about 4 millimeters to about 15 millimeters.

17. The dispersible moist wipe set forth in claim 12 wherein the regenerated fibers have a length in the range of about 6 millimeters to about 12 millimeters.

18. The dispersible moist wipe set forth in claim 12, wherein the web has a formation value of at least 16.

19. A dispersible moist wipe comprising a nonwoven tissue web comprising regenerated fibers having a length in the range of about 4 millimeters to about 15 millimeters and natural fibers having a length greater than about 1 millimeter, wherein the regenerated fibers and the natural fibers are hydroentangled using an energy within a range between about 0.12 kw-hr/kg and about 0.9 kw-hr/kg such that the web has a geometric mean tensile strength of at least 150 grams per inch, the nonwoven tissue web being free of a binder and having a formation value of at least 12, wherein the nonwoven tissue web has at least one ribbon-like structure extending along the nonwoven tissue web, and at least one hole in the nonwoven tissue web positioned adjacent the at least one ribbon-like structure, the at least one ribbon-like structure defining an area of higher entanglement of the regenerated fibers and the natural fibers than in other areas of the nonwoven tissue web.

20. The dispersible moist wipe set forth in claim 19 wherein the web has a machine direction tensile strength of at least 240 grams per inch.

21. The dispersible moist wipe set forth in claim 19 wherein the web has a machine direction tensile strength of at least 300 grams per inch.

22. The dispersible moist wipe set forth in claim 19 wherein the web comprises regenerated fibers in an amount of about 10 to about 20 percent by weight and natural fibers in an amount of about 80 to about 90 percent by weight.

23. The dispersible moist wipe set forth in claim 19 wherein the regenerated fibers have a length in the range of about 6 millimeters to about 12 millimeters.

24. The dispersible moist wipe set forth in claim 19 wherein the web has a formation value of at least 16.

25. The dispersible moist wipe set forth in claim 1 wherein the at least one ribbon-like structure comprises a plurality a ribbon-like structures.

26. The dispersible moist wipe set forth in claim 25 wherein each ribbon-like structure of the plurality of ribbon-like structures is generally parallel to the other ribbon-like structures.

27. The dispersible moist wipe set forth in claim 12 wherein the at least one ribbon-like structure comprises a plurality a ribbon-like structures.

28. The dispersible moist wipe set forth in claim 27 wherein each ribbon-like structure of the plurality of ribbon-like structures is generally parallel to the other ribbon-like structures.

29. The dispersible moist wipe set forth in claim 19 wherein the at least one ribbon-like structure comprises a plurality a ribbon-like structures.

30. The dispersible moist wipe set forth in claim 29 wherein each ribbon-like structure of the plurality of ribbon-like structures is generally parallel to the other ribbon-like structures.

* * * * *